US008688474B2

(12) United States Patent
Walter et al.

(10) Patent No.: US 8,688,474 B2
(45) Date of Patent: Apr. 1, 2014

(54) PATIENT HEALTH RECORD ACCESS SYSTEM

(75) Inventors: Ervin Walter, Madison, WI (US); Mukesh Allu, Madison, WI (US); Scott A. Lordi, Madison, WI (US); Gary S. Holmes, North Freedom, WI (US); Carl D. Dvorak, Madison, WI (US); Joel E. Rod, Madison, WI (US); Sumit S. Rana, Madison, WI (US); Samit Govind Sureka, Madison, WI (US); Aaron T. Cornelius, Mount Horeb, WI (US)

(73) Assignee: Epic Systems Corporation, Verona, WI (US)

( * ) Notice: Subject to any disclaimer, the term of this patent is extended or adjusted under 35 U.S.C. 154(b) by 1913 days.

(21) Appl. No.: 09/821,615

(22) Filed: Mar. 29, 2001

(65) Prior Publication Data

US 2003/0208381 A1 Nov. 6, 2003

Related U.S. Application Data

(60) Provisional application No. 60/214,290, filed on Jun. 26, 2000.

(51) Int. Cl.
  *G06Q 50/00* (2012.01)
  *G06Q 10/00* (2012.01)
(52) U.S. Cl.
  USPC .................................................. 705/3; 705/2
(58) Field of Classification Search
  USPC .......................................... 705/2–4; 709/203
  See application file for complete search history.

(56) References Cited

U.S. PATENT DOCUMENTS

| 4,591,974 | A | 5/1986 | Dornbush et al. |
| 4,667,292 | A | 5/1987 | Mohlenbrock et al. |
| 4,839,806 | A | 6/1989 | Goldfischer et al. |
| 4,893,270 | A | 1/1990 | Beck et al. |
| 4,962,475 | A | 10/1990 | Hernandez et al. |
| 5,072,383 | A | 12/1991 | Brimm et al. |

(Continued)

FOREIGN PATENT DOCUMENTS

| WO | WO-96/27163 A1 | 9/1996 |
| WO | WO-98/13783 | 4/1998 |

(Continued)

OTHER PUBLICATIONS

Mercando, A. D., Appointment Scheduling on Computer, PACE, Jul. 1997, pp. 1860-1862, vol. 20.

(Continued)

*Primary Examiner* — Robert Morgan
*Assistant Examiner* — Kristine Rapillo
(74) *Attorney, Agent, or Firm* — Boyle Fredrickson, S.C.

(57) ABSTRACT

An integrated system provides patients with secure, real-time access to their Personal Health Record and an Enterprise Health Information System (PHR and EHIS, respectively). Access may be provided by way of the Internet and via a Personal Health Portal (PHP) web page. From the secure PHP web page, patients can view information created and maintained by their health care providers and their affiliated staff. The patients can also request services and information from their health care providers and affiliated staff, directly access EHIS-related services, such as scheduling an appointment, scheduling, paying a bill, enrolling in a class, completing insurance and other forms, and viewing information and Internet services that are relevant to their particular health status.

18 Claims, 10 Drawing Sheets

(56) References Cited

U.S. PATENT DOCUMENTS

| | | | |
|---|---|---|---|
| 5,072,412 A | 12/1991 | Henderson, Jr. et al. |
| 5,072,838 A | 12/1991 | Price, Jr. et al. |
| 5,077,666 A | 12/1991 | Brimm et al. |
| 5,088,981 A | 2/1992 | Howson et al. |
| 5,101,476 A | 3/1992 | Kukla |
| 5,253,362 A | 10/1993 | Nolan et al. |
| 5,301,105 A | 4/1994 | Cummings, Jr. |
| 5,319,543 A | 6/1994 | Wilhelm |
| 5,325,478 A | 6/1994 | Shelton et al. |
| 5,361,202 A | 11/1994 | Doue |
| 5,428,778 A | 6/1995 | Brookes |
| 5,471,382 A | 11/1995 | Tallman et al. |
| 5,546,580 A | 8/1996 | Seliger et al. |
| 5,557,515 A | 9/1996 | Abbruzzese et al. |
| 5,574,828 A | 11/1996 | Hayward et al. |
| 5,596,752 A | 1/1997 | Knudsen et al. |
| 5,603,026 A | 2/1997 | Demers et al. |
| 5,666,492 A | 9/1997 | Rhodes et al. |
| 5,692,125 A | 11/1997 | Schloss et al. |
| 5,724,584 A | 3/1998 | Peters et al. |
| 5,740,800 A | 4/1998 | Hendrickson et al. |
| 5,748,907 A | 5/1998 | Crane |
| 5,751,958 A | 5/1998 | Zweben et al. |
| 5,758,095 A | 5/1998 | Albaum et al. |
| 5,760,704 A | 6/1998 | Barton et al. |
| 5,772,585 A | 6/1998 | Lavin et al. |
| 5,778,346 A | 7/1998 | Frid-Nielsen et al. |
| 5,781,442 A | 7/1998 | Engleson et al. |
| 5,781,890 A | 7/1998 | Nematbakhsh et al. |
| 5,802,253 A | 9/1998 | Gross et al. |
| 5,823,948 A | 10/1998 | Ross, Jr. et al. |
| 5,832,450 A | 11/1998 | Myers et al. |
| 5,833,599 A | 11/1998 | Schrier et al. |
| 5,838,313 A | 11/1998 | Hou et al. |
| 5,842,976 A | 12/1998 | Williamson |
| 5,845,253 A | 12/1998 | Rensimer et al. |
| 5,848,393 A | 12/1998 | Goodridge et al. |
| 5,848,395 A | 12/1998 | Edgar et al. |
| 5,850,221 A | 12/1998 | Macrae et al. |
| 5,867,688 A | 2/1999 | Simmon et al. |
| 5,867,821 A | 2/1999 | Ballantyne et al. |
| 5,899,998 A | 5/1999 | McGauley et al. |
| 5,915,240 A | 6/1999 | Karpf |
| 5,924,074 A | 7/1999 | Evans |
| 5,929,851 A | 7/1999 | Donnelly |
| 5,946,659 A | 8/1999 | Lancelot et al. |
| 5,960,406 A | 9/1999 | Rasansky et al. |
| 5,974,389 A | 10/1999 | Clark et al. |
| 5,983,210 A | 11/1999 | Imasaki et al. |
| 5,987,498 A * | 11/1999 | Athing et al. ................ 709/203 |
| 5,997,446 A | 12/1999 | Stearns |
| 5,997,476 A | 12/1999 | Brown |
| 5,999,916 A | 12/1999 | Peters et al. |
| 6,014,631 A | 1/2000 | Teagarden et al. |
| 6,016,477 A | 1/2000 | Ehnebuske et al. |
| 6,021,404 A | 2/2000 | Moukheibir |
| 6,029,138 A | 2/2000 | Khorasani et al. |
| 6,037,940 A | 3/2000 | Schroeder et al. |
| 6,047,259 A | 4/2000 | Campbell et al. |
| 6,063,026 A | 5/2000 | Schauss et al. |
| 6,067,523 A | 5/2000 | Bair et al. |
| 6,081,786 A | 6/2000 | Barry et al. |
| 6,082,776 A | 7/2000 | Feinberg |
| 6,139,494 A | 10/2000 | Cairnes |
| 6,154,726 A | 11/2000 | Rensimer et al. |
| 6,182,047 B1 | 1/2001 | Dirbas |
| 6,188,988 B1 | 2/2001 | Barry et al. |
| 6,233,616 B1 * | 5/2001 | Reid ............................ 709/225 |
| 6,263,330 B1 | 7/2001 | Bessette |
| 6,275,150 B1 | 8/2001 | Mandler et al. |
| 6,283,761 B1 | 9/2001 | Joao |
| 6,289,368 B1 | 9/2001 | Dentler et al. |
| 6,304,905 B1 | 10/2001 | Clark |
| 6,317,719 B1 | 11/2001 | Schrier et al. |
| 6,332,167 B1 | 12/2001 | Peters et al. |
| 6,345,260 B1 | 2/2002 | Cummings, Jr. et al. |
| 6,401,072 B1 | 6/2002 | Haudenschild et al. |
| 6,415,275 B1 | 7/2002 | Zahn |
| 6,523,009 B1 * | 2/2003 | Wilkins ............................ 705/3 |
| 6,725,200 B1 * | 4/2004 | Rost ................................ 705/3 |
| 6,757,898 B1 * | 6/2004 | Ilsen et al. .................... 709/203 |
| 6,988,075 B1 * | 1/2006 | Hacker ............................ 705/3 |
| 2001/0016056 A1 | 8/2001 | Westphal et al. |
| 2001/0016853 A1 | 8/2001 | Kucala |
| 2001/0041991 A1 * | 11/2001 | Segal et al. ...................... 705/3 |
| 2001/0049610 A1 | 12/2001 | Hazumi ............................ 705/3 |
| 2001/0051888 A1 | 12/2001 | Mayhak, Jr. et al. |
| 2001/0056433 A1 | 12/2001 | Adelson et al. |
| 2002/0001375 A1 | 1/2002 | Alcott et al. |
| 2002/0001387 A1 | 1/2002 | Dillon |
| 2002/0002473 A1 | 1/2002 | Schrier et al. |
| 2002/0002535 A1 | 1/2002 | Kitchen et al. |
| 2002/0007287 A1 | 1/2002 | Straube et al. |
| 2002/0062229 A1 | 5/2002 | Alban et al. |
| 2002/0065682 A1 * | 5/2002 | Goldenberg .................... 705/2 |
| 2002/0188478 A1 | 12/2002 | Breeland et al. |
| 2003/0061072 A1 | 3/2003 | Baker et al. |
| 2003/0110059 A1 | 6/2003 | Janas, III et al. |

FOREIGN PATENT DOCUMENTS

| | | |
|---|---|---|
| WO | WO-99/22330 A1 | 5/1999 |
| WO | WO-99/41682 A2 | 8/1999 |
| WO | WO-99/44162 A1 | 9/1999 |
| WO | WO-99/63473 A1 | 12/1999 |
| WO | WO-00/28460 | 5/2000 |
| WO | WO-00/29983 | 5/2000 |
| WO | WO-00/65522 A2 | 11/2000 |
| WO | WO-02/29664 A1 | 4/2002 |

OTHER PUBLICATIONS

Michihiro Hazumi and Toshio Kawamoto, "Development of Electronic Medical Record System," *NEC Res. & Develop.*, vol. 41, pp. 102-105, Jan. 2000.

"Sunrise Knowledge-Based Orders," Advanced Clinical Solutions, ECLIPSYS, www.eclipsys.com, Dec. 2002, 4 pages.

"Sunrise Clinical Manager," Advanced Clinical Solutions, ECLIPSYS, www.eclipsys.com, Dec. 2002, 4 pages.

"News & events," ECLIPSYS, www.eclipsys.com, Apr. 16, 2002, 3 pages.

"Horizon Clinicals," McKesson Corporation, www.mckesson.com, 2003, 2 pages.

"Acute Care EMR—Solutions," Cerner Corporation, www.cerner.com, 2002-2003, 2 pages.

"Foundation," IDX Systems Corporation, www.idx.com, 1999-2004, 2 pages.

"Supporting the Work of Clinicians," IDX Systems Corporation, www.idx.com, 1999-2004, 1 page.

"Autonomy Update™", Product Brief, Autonomy Inc., www.autonomy.com, Mar. 2003, 2 pages.

"Brio.Portal", Sun Solutions Catalog, Sun Microsystems, www.sun.com, 1994-2002, 1 page.

"Portal-in-a-Box™," Product Brief, Autonomy Inc., www.automony.com, Apr. 2002, 6 pages.

"Actuate Software," Sun Solutions Catalog, Actuate Corporation & Sun Microsystems, www.sun.com, 2002, 24 pages.

McDonald et al., "The Regenstrief Medical Record System: a quarter century experience," International Journal of Medical Informatics, vol. 54, 1999, pp. 225-253.

"CDR-Web," Reliance Software Systems, Website, 2000, 1 page.

Marietti, "'O' Pioneers!," Healthcare Informatics, Website, May 1999, 9 pages.

Johnson, "Today's CDRs: The Elusive Complete Solution," Healthcare Informatics, (Website), Jul. 1997, 7 pages.

Andrew et al., "Computer-Based Patient Records—Venturing Off the Beaten Path: It's Time to Blaze New CPR Trails," Healthcare Informatics, (Website), May 1997, 17 pages.

"EMR Features," Care is #1, 1999-2000, 1 page.

(56) References Cited

OTHER PUBLICATIONS

"Enterprise Systems Management," Cerner Corporation, www.cerner.com, Sep. 13, 2001, 5 pages.
"HealthMatics™ Office", Healthmatics Office, Website, 3 pages, (date unknown).
Clinicomp, Intl., Website, 1999-2000, 1 page.
"ExcelCare Windows", Website, 2 pages (date unknown).
"IC-Chart Information", INTEGREAT, Website, 1 page, (date unknown).
"Managing mail messages with rules," Microsoft Outlook Help Manual, Website, Version 6, 5 pages Jun. 24, 2002.
EncounterPRO, the Workflow Enabled CPR/EMR from JMJ Technologies, JMJ Technologies, Inc., www.jmjtech.com, Nov. 8, 2002, 6 pages.
"Expeditor Systems—The Patient Flow Systems Experts", Expeditor Systems, www.expeditor.com, 2001, 3 pages.
"Working with Patient Lists," EpicCare Inpatient Electronic Medical Record Jul. 2000 User's Guide, Epic Systems Corp., Section 10.5-10.6, 3 pages.
"Patient Lists," EpicCare Inpatient Electronic Medical Record Jul. 2000 User's Guide, Epic Systems Corp., Section 11.3-11.4, 3 pages.
"Oacis—Census Management," Dinmar (U.S.) Inc., www.oacis.com, 2002, 2 pages.
Grimson et al., "Interoperability Issues in Sharing Electronic Healthcare Records—the Synapses Approach," IEEE, 1997, pp. 180-185.
"Clinician Documentation with EMR," Clinicomp, Intl., www.clinicomp.com, 1999-2002, 1 page.
"Essentris™ CPOE", Clinicomp, Intl., www.clinicomp.com, 1999-2002, 2 pages.
"Essentris™ GDR," Clinicomp, Intl., www.clinicomp.com, 1999-2002, 2 pages.
"Intensivist Tools," Clinicomp, Intl., www.clinicomp.com, 1999-2002, 2 pages.
"CMRxp—Computerized Medical Records Powered by Experience!!," Electronic Medical Records (EMR)xp Experience, Chartcare, Inc., www.chartcare.com, Mar. 5, 2003, 2 pages.
"Dr-InBasket-Lab Results, Messaging and To-Do's," Chartcare, Inc., www.chartcare.com, Mar. 5, 2003, 3 pages.
"PatInfo-Patient Information Handouts," PatInfo-Patient Demographics Software, Chartcare, Inc., www.chartcare.com, Mar. 5, 2003, 2 pages.
"Recall-Patient Health Maintenance," Chartcare, Inc., www.chartcare.com, Mar. 5, 2003, 3 pages.
"LabTrack-Lab Ordering & Results Tracking," LabTrack-Lab Result Tracking Software, Chartcare, Inc., www.chartcare.com, Mar. 5, 2003, 3 pages.
"Rx-MedTrack-Prescription Writing/Medication Tracking," Rx-MedTrack-Prescription Writing Software, Chartcare, Inc., www.chartcare.com, Mar. 5, 2003, 2 pages.
"The Right Tools," Product Description, Integreat Inc., www.igreat.com, 2003, 1 page.
"IC-Chart Additional Modules," Integreat Inc., www.igreat.com, 2003, 2 pages.
"Services," Integreat Inc., www.igreat.com, 2003, 2 pages.
International Search Report for Application No. PCT/US01/20357 dated Aug. 1, 2003.
Egan et al., "Computers and Networks in Medical and Healthcare Systems," Comput. Biol. Med., vol. 23, No. 3, 1995, pp. 355-365.
Plaisant et al., "An Information Architecture to Support the Visualization of Personal Histories," Information Processing & Management, vol. 34, No. 5, 1998, pp. 581-597.
Van De Velde, "Framework for a Clinical Information System," International Journal of Medical Informatics, vol. 57, 2000, pp. 57-72.
Fabbretti et al., "Applying the Object Paradigm to a Centralized Database for a Cardiology Division," International Journal of Bio-Medical Computing, vol. 42, 1996, pp. 129-134.
"HCS Order Communications Module," web.archive.org/hcsinteractant.com, 2000, pp. 1-3.
Ebidia et al., "Getting Data Out of the Electronic Patient Record: Critical Steps in Building a Data Warehouse for Decision Support," SIMS University Health Network, Dept. of Medicine, University of Toronto, Canada, Nov. 8, 1999, pp. 1-5.
"Patient1 Vista", PerSe Technologies, www.per-se.com/web.archive.org, 2000, 2 pages.
"Sunrise Clinical Manager", Eclipsys, Sunrise Clinical Overview, www.eclipsnet.com/web.archive.org, 1999, 1 page.
"American Medical Management Selects Tandem Computers as Systems Partner", PR Newswire, Feb. 20, 1997, 2 pages.
"Premier Members Select Cerner's Clinical Data Repository as a Result of Exclusive Endorsement", PR Newswire, Feb. 19, 1997, 2 pages.
"Physicians and Staff Go Online with Cerner's Clinical Data Repository and Orders Management", PR Newswire, Mar. 4, 1996, 2 pages.
"Patient1", PerSe Technologies, www.per-se.com/web.archive.org, 2000, 4 pages.

\* cited by examiner

PATIENT HEALTH RECORD ACCESS SYSTEM

CROSS-REFERENCE TO RELATED APPLICATIONS

This coninuation applications claims priority to U.S. Provisional Patent Application Ser. No. 60/214,290, entitled "Integrated Patient and Enterprise Health Record System," filed Jun. 26, 2000, the disclosure of which is hereby expressly incorporated herein by reference.

FIELD OF THE INVENTION

The present invention relates generally to health records management, and more particularly, to a system for providing a patient with access to the patient's health record.

BACKGROUND OF THE INVENTION

A variety of Internet-based systems for providing access to a patient's health record and related healthcare information have been proposed. Such Internet-based personal or patient medical records either provide patients access only to information that they enter and maintain themselves, or provide them with delayed and limited access to information contained in a separate healthcare information system from which patient health information must be abstracted and uploaded to a web server in regularly scheduled batch processes. A patient is unsure if the information they are viewing is the most up to date and complete. Apart from the ability to view selected portions of information or patient self-generated information, the proposed systems have not provided an effective forum to allow the patient to communicate with their health care providers. None of the proposed systems feature secured, real-time access to an integrated patient health record.

Thus, there is a need for a patient health record access system that provides real-time communication between the patient and an integrated Patient Health Record (PHR) and an Enterprise Health Information System (EHIS). Such a system would provide patients with the most up-to-date information. Moreover, patients could avail themselves of electronic health-related services in real-time. Furthermore, a real-time, integrated PHR/EHIS system could provide efficiency, workflow flexibility and connectivity between patients and their health care providers and affiliated staff that are not available using previously disclosed systems.

DETAILED DESCRIPTION OF THE PREFERRED EMBODIMENTS

An integrated system provides patients with secure, real-time access to their Personal Health Record and an Enterprise Health Information System (PHR and EHIS, respectively). Access may be provided by way of the Internet and via a Personal Health Portal (PHP) web page. From the secure PHP web page, patients can view information created and maintained by their health care providers and their affiliated staff. The patients can also request services and information from their health care providers and affiliated staff, directly access EHIS-related services, such as scheduling an appointment, paying a bill, enrolling in a class, completing insurance and other forms, and viewing information and Internet services that are relevant to their particular health status.

In a preferred embodiment of the invention a patient health record data server, including a machine-readable media having a data structure containing patient-created data, is coupled by a communication network with a patient interface. The communication network may be the Internet and the patient interface may be a suitable Internet access device including a browser for supporting a personalized web page. A secure interface securely couples, in real-time, the patient health record server to an enterprise health record system for providing access by the patient to patient-related data retained within the enterprise health record system. Thus, the patient, via the patient interface, may access the patient health record server for manipulating the patient-created data and for accessing the patient-related data from the enterprise health record system.

While described in terms of several preferred embodiments, it will be appreciated that the invention is not limited in scope to the embodiments herein described. Many modifications, alterations and additions may be made without departing from the fair scope of the invention.

Figure 1:
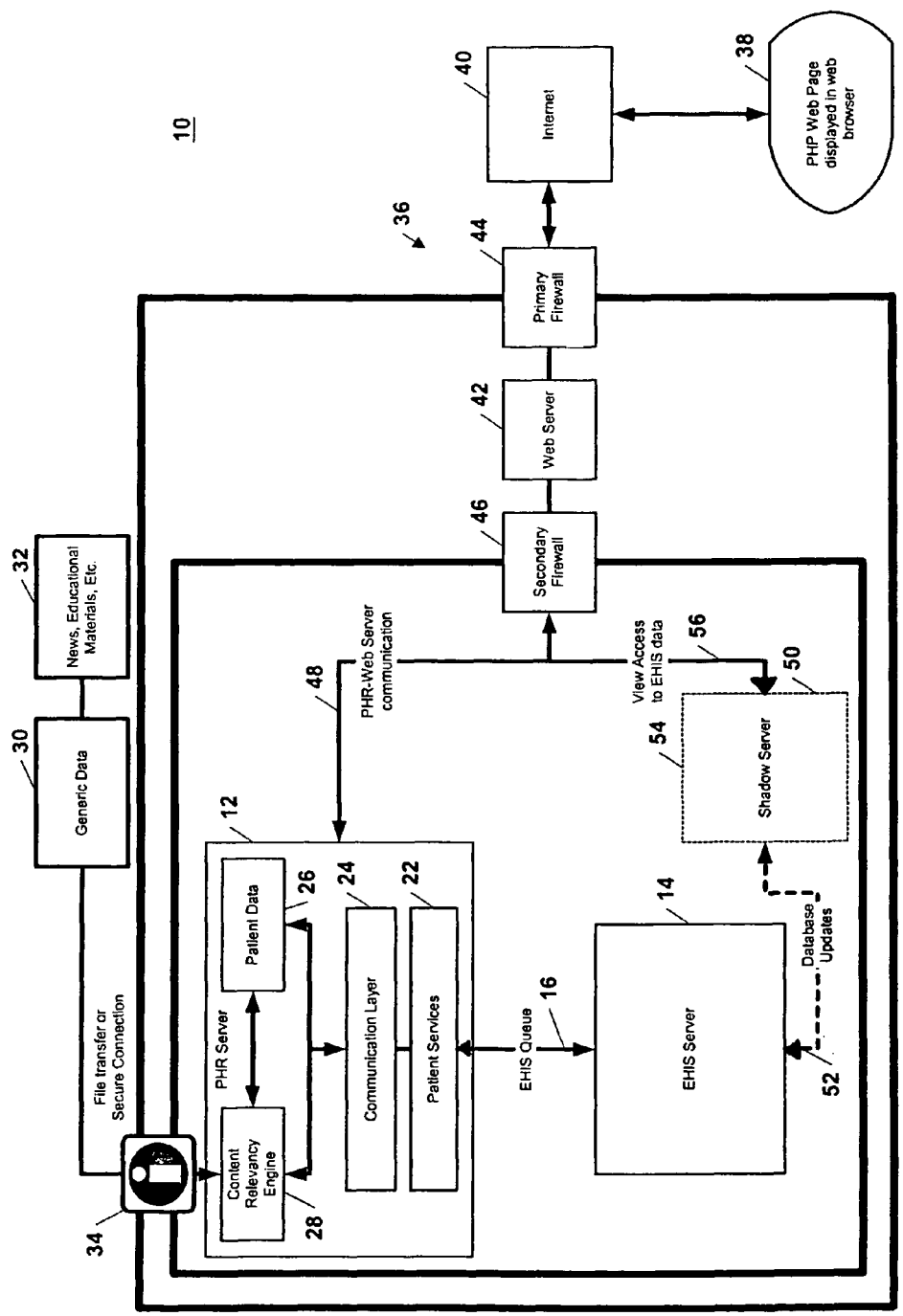
FIG. 1 is a system block diagram of a patient health record access system in accordance with a preferred embodiment of the invention.

Referring to FIG. 1 of the drawings, a patient access system 10 includes a Patient Health Record (PHR) data server 12 and an EHIS data server 14. The PHR data server 12 may be any suitable platform including processing, memory and data storage capability to perform the functions herein described. The PHR data server 12 stores data entered by the patient within a data structure configured within the storage portion of the PHR data server 12. A secure interface or EHIS queue 16 securely couples the PHR server 12 and the EHIS data server 14 for communication of data and information from the PHR data server 12 to the EHIS data server 14. The EHIS Queue 16 provides a real-time secure communication link for information moving from the PHR data server 12 to the EHIS data server 14. This queue is used to transfer information for secure messaging and self-service options. In response to information received from the PHP web page, the PHR data server 12 forwards information to the EHIS queue 16. Information in the EHIS queue 16 is then processed appropriately by the EHIS data server 14.

While the specific configuration of the EHIS data server 14 is not particular to the structure and function of the present invention, preferably, the EHIS data server 14 is a single data repository structured to support both the separation and the sharing of data. As such, the EHIS data server 14 may receive information from existing outpatient and inpatient data management systems via interfaces or from various integrated applications. The EHIS data server 14 may be configured to organize information into a consistent whole to provide a longitudinal patient record. For example, the EHIS data server 14 may be linked to manage all aspects of a patient's hospital health status and care and to support effective management of patient lists, results inquiry management, complete clinical documentation, physician order entry with decision support, nursing workflow and documentation, and discharge planning. The EHIS data server 14 may further be configured to support the inclusion of problem lists, order communications, results reporting, pharmacy management, quick documentation, clinical messaging and communication. Additionally, the EHIS data server may be configured to manage referral information, up-to-date progress notes, lab results, discharge instructions, portions of a patient's record, and emergency summary cards. A suitable data management product that may be adapted as the EHIS data server 14 is the Epicenter® Enterprise Data Repository and related suite of products available from Epic System Corporation of Madison, Wis.

The PHR data server 12 includes a patient services application layer 22, a communication layer 24, a patient data manager 26 and a content relevancy engine 28, all of which are suitably linked within an architecture for operation under the direction of the PHR data server 12. The patient data manager 26 includes suitable storage capability, such as magnetic, optical, or other storage technology, for storing patient-created data. The patient services application layer 22 and the communication layer 24 include routines for managing access and use of the patient-created data, as well as to provide patient services. The PHR data server 12 is further linked, by way of the content relevancy engine 28 to a source of generic data 30 and a source of news, educational and similar materials 32 via a secure connection 34, such as a Internet protocol secure (IPsec) connection or by a file transfer protocol (ftp) connection.

A communication network 36 couples the PHR data server 12 to a patient interface 38. The communication network 36 may include the Internet 40 or other suitable data network, and the PHR data server 12 is linked to the Internet 40 by a web server 42 in a highly secure dual firewall configuration. In this arrangement, a primary fire wall 44 protects the web server 42 and a secondary fire wall 46 protects the PHR data server 12 and the EHIS data server 14 with a communication link 48 coupling the communication network 36 to the PHR data server 12.

In a preferred embodiment of the invention, a shadow server 50 is provided and maintains a copy of at least the patient-related data retained within the EHIS data server 14. A communication link 52 permits the copying of the patient-related data from the EHIS data server 14 to the shadow server 50, and a view access only communication link 56 couples the shadow server 50 to the communication network 36, and hence to the patient interface 38. This arrangement advantageously allows the EHIS data server 14 to be highly available for EHIS systems operation. Alternatively, the communication network 36 may be directly linked to the EHIS data server 14.

Patients access the system 10 by logging into the web server 42 via the patient interface 38. The patient interface 38 is preferably configured as a web page displayed within a web browser running on a suitable platform, and is further preferably configured as a personalized Personal Health Portal (PHP) web page providing the patient with patient-specific information and links to the features and services offered by the invention. The web server 42 may be any suitable web server platform containing routines for displaying the PHP web page and for managing online communication between a user logged in via an associated PHP web page and the PHR data server 12 and the EHIS data server 14.

A user logging into the system via the PHP web page may or may not be an existing patient of the healthcare enterprise. For existing patient users, the PHR data server 12 may already contain a record for the patient and, as will be described, the user is provided access to the information contained in that record. Some existing patients and new patients may not have a record within the PHR data server 12. These patients will have at least two options for gaining access to the functionality of the system 10. First, the patient may fully register by providing appropriate identifying. The PHR data server 12 creates a patient record for the user.

A patient may gain access without fully identifying himself or herself. The patient may enter patient data using a user name and identifying information that is anonymous in nature. Access for this "anonymous user" may be limited to predefined functionality. For example, the anonymous user may be permitted only to view information related to services provide by the healthcare enterprise, may be able to create a record or patient created information within the PHR data server 12, may be able to ask questions of the healthcare enterprise and receive responses, and the like. The anonymous user, however, would not be permitted to make appointments or request specific services of the healthcare enterprise. Additionally, should the anonymous user become a patient of the healthcare enterprise, the PHR data server 12 may use the anonymous user record to create a patient record within the PHR data server 12 without requiring the patient to reenter information.

Figure 2:
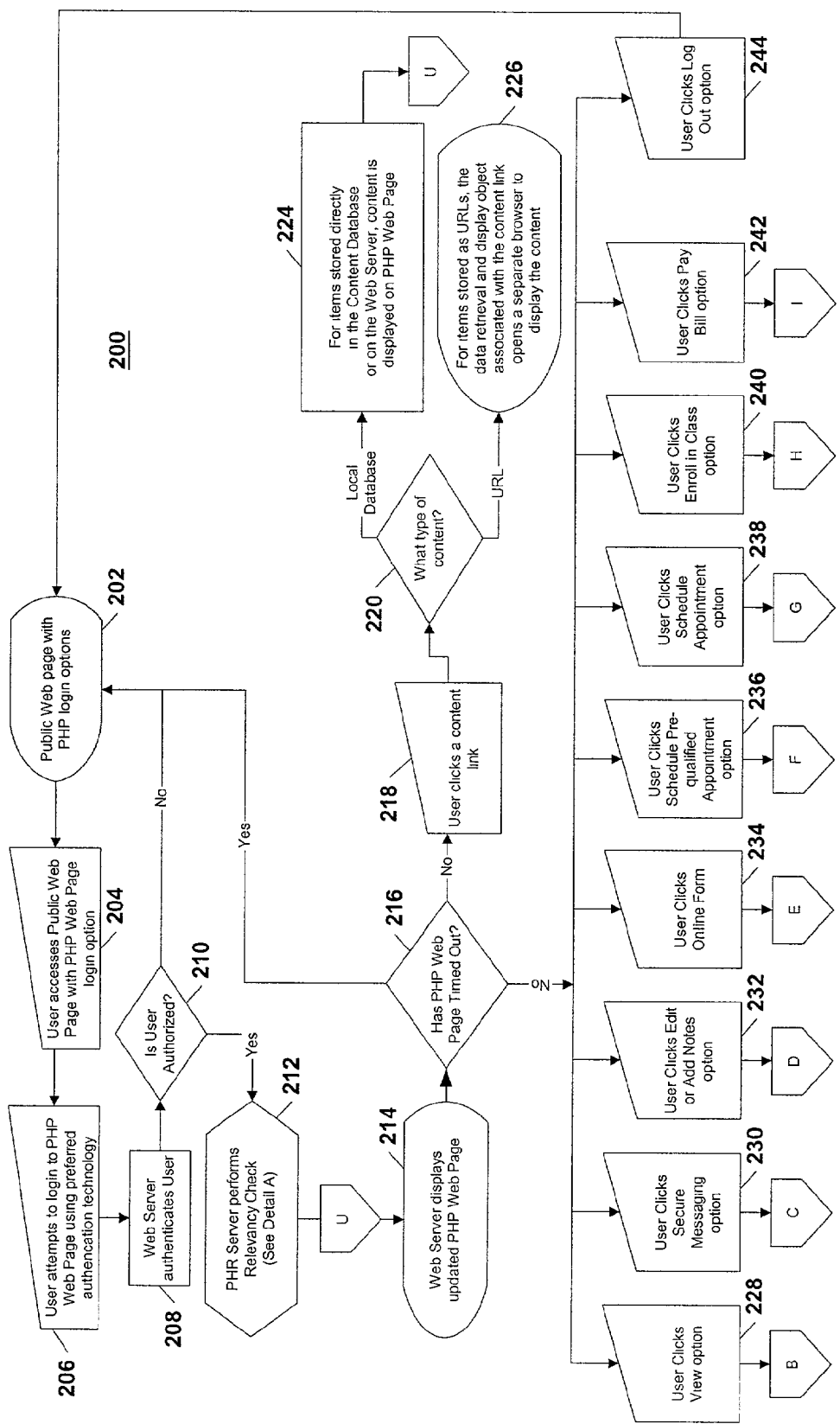
FIG. 2 is a flowchart illustrating operation of the system illustrated in FIG. 1.

Operation and use of the system is described in more detail with reference to FIGS. 2-10. The flowcharts depicted in FIGS. 2-10 are linked and illustrate the operation of the system 10 in accordance with a preferred embodiment of the invention. The alpha designations indicate the interconnections between the various flowcharts depicted in the figures. Turning to FIG. 2 depicted is a method 200 of providing access by a patient to the PHR data server 12 and the EHIS data server 14. The method 200 begins at step 202 where the patient accesses a public web page, such as an Internet service provider (ISP) home page, with a PHP web page option and selects the PHP web page option, step 204. At step 206, the user attempts to log into the PHP web page, which is provided by the web server 42, using a suitable authentication technology. The web server 42 executes the authentication routine at step 208, and a user authorization determination is made at step 210. If the user is not authorized, the user is returned to the public web page. If the user is authorized, the content relevancy engine 28 functions, step 212, as will be described in connection with FIG. 3, and at step 214, the web server 42 generates and displays the user's PHP web page on the patient interface 38.

From the PHP web page, the user is provided a selection of links providing access to patient-relevant content, information from the patient's enterprise health record, and services associated with the enterprise health information system. If the user does not click on a link within a timeout period causes the web server 42, at step 216, to log the user out and to return the user to the public page.

At step 218 the user clicks a content link. Depending on the type of content selected by the user, step 220, if the item is stored directly in a content database or on the web server 42, at step 224 the content is displayed on the PHP web page. Otherwise, for items stored as URLs, at step 226 the data retrieval and display option associated with the link opens a separate browser page to display the content.

In a preferred embodiment of the invention, the user may also select: a view option; a secure messaging option, an edit or add notes option; an online form; schedule a prequalified appointment option; schedule an appointment option; enroll in a class option; pay a bill option or log out, respectively, links associated with blocks 228-244.

Figure 3:
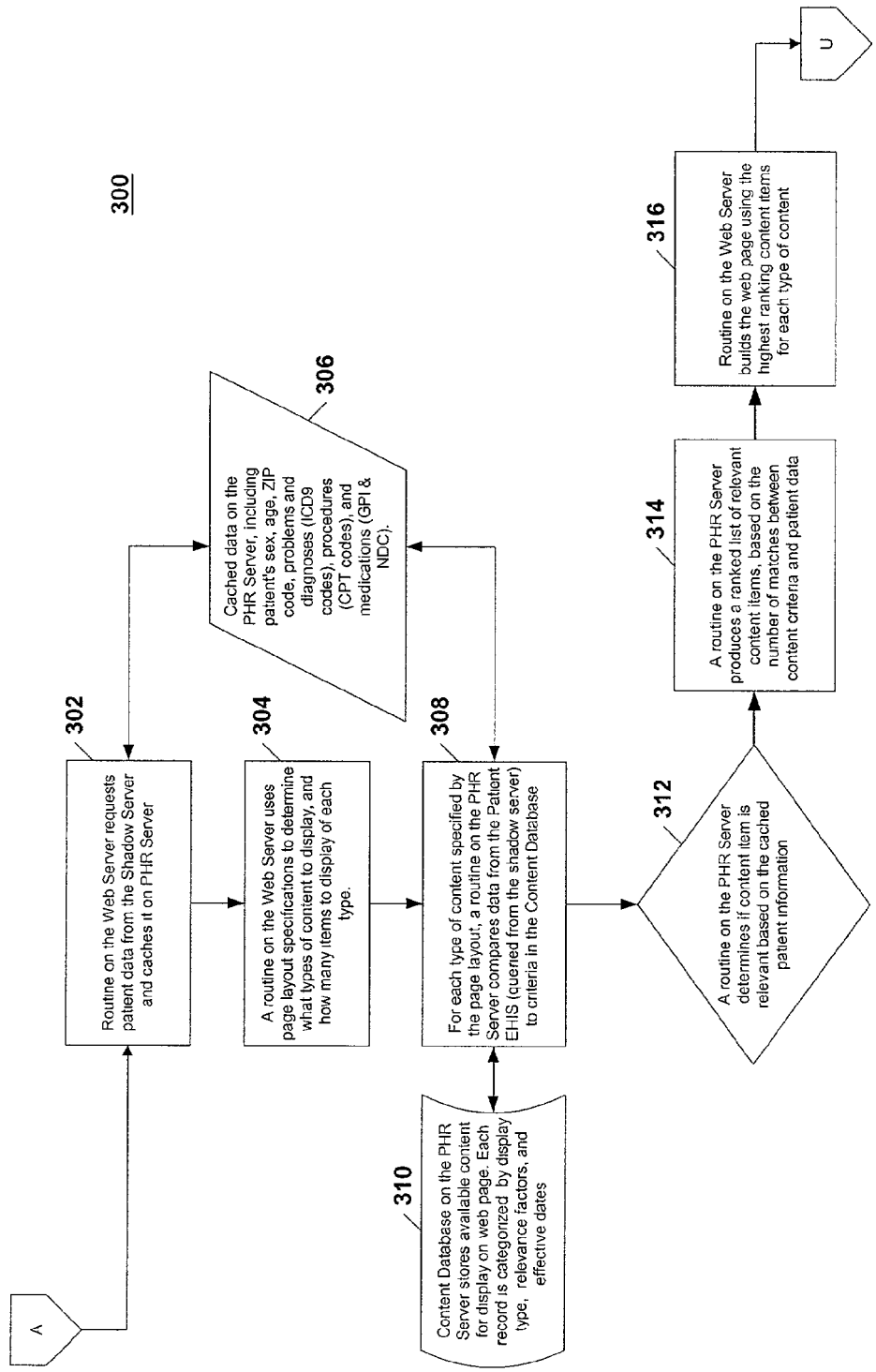
FIG. 3 is a flowchart illustrating operation of a content relevancy engine portion of the system illustrated in FIG. 1.
Figure 4:
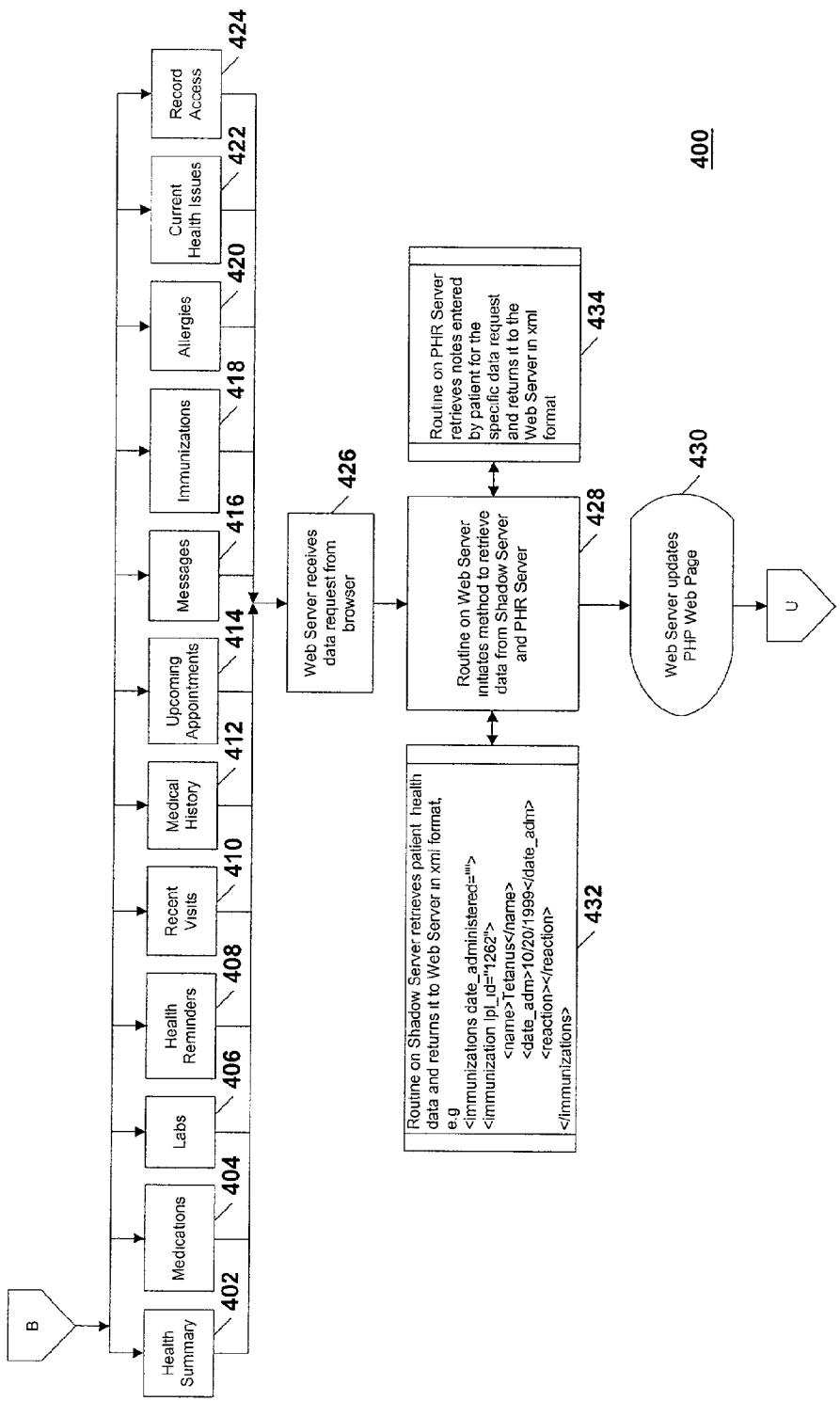
FIG. 4 is a flowchart illustrating operation of the system illustrated in FIG. 1 for viewing of information by the patient.
Figure 5:
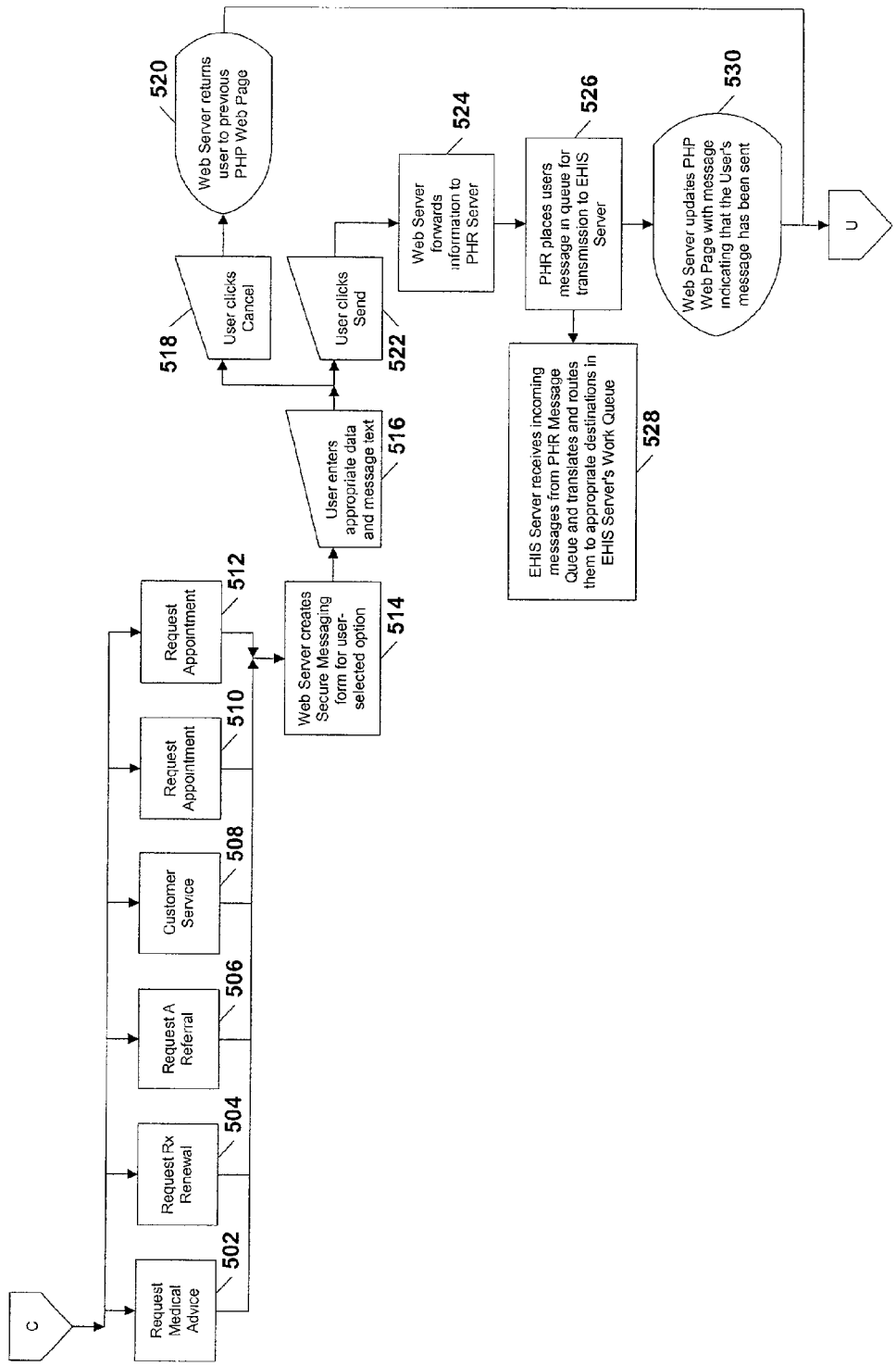
FIG. 5 is a flowchart illustrating operation of the system illustrated in FIG. 1 for processing messages.
Figure 6:
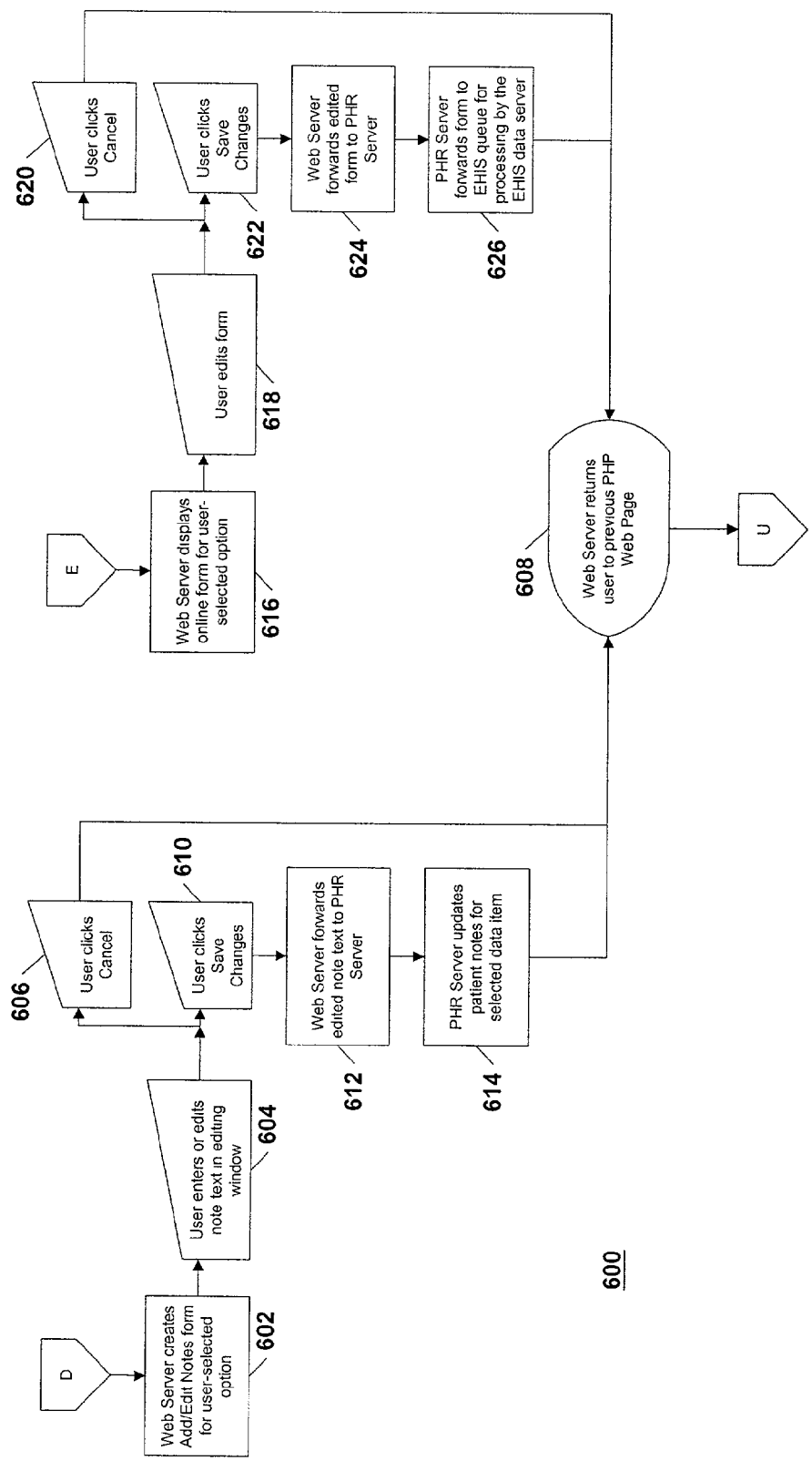
FIG. 6 is a flowchart illustrating operation of the system illustrated in FIG. 1 for accepting and recording information from a patient.

Referring now to FIG. 3, the content relevancy engine 28 operates in accordance with a method 300 depicted therein. At step 302, the web server 42 requests patient-related information from the Shadow Server 14 and caches it on the PHR data server 12. This data includes the user's sex, age, zip code, medical problems and diagnoses (using ICD9 codes), procedures (using CPT codes) and medications (using GPI & NDC) as indicated at block 306. At step 304, another routine on the PHR data server 12 uses page layout specifications associated with the user's PHP web page, which may be specified by the system provider or may be user configurable, to determine what types of content to display, and how many items to display of each type. At step 308, for each type of content specified by the page layout, a routine within the content relevancy engine 28 compares the patient-related data to criteria in the content database. The content database is maintained on the PHR data server 12 and stores available content for display on the PHP web page with each record being categorized by display type, relevance factors, and effective dates as indicated at block 310. The content relevancy engine 28 at step 312 then determines if a content item is relevant based upon the cached patient-related information. At step 314, the content relevancy engine 28 then produces a ranked list of relevant content items, based on a number of matches between the content criteria and the patient-related information. Then, at step 316, the web server 42 builds the PHP web page according to the page layout (step 308), using the highest-ranking content items for each type of content.

When the user selects a link associated with a view option, secure messaging option, or self-service option, the PHR data server 12 initiates a routine associated with the link. Link 228 in FIG. 2 initiates a view content routine 400 illustrated in FIG. 4. The system 10 advantageously permits viewing of a wide variety of information types including patient-created information stored within the PHR data server 12 and patient-related information stored within the EHIS data server 14. The patient-created data may be notes and comments relating to the user's health or requests for information. The patient-related information may be portions of the user's medical record and other information created by the health care professionals and staff. In the preferred embodiment illustrated in FIG. 4, the user may select to view a health summary, a medication list, lab results, health reminders, recent visit information, medical history, upcoming appointments, messages, immunization information, allergies information, current health issues, financial and insurance information, and records access by selecting an appropriate link associated with the requested information represented by blocks 402-424, respectively. Upon the user selecting the link, at step 426 the web server 42 receives the data request, and at step 428 initiates a routine to retrieve the requested information, either from the PHR data server 12 or the shadow server 50 (or EHIS data server 14 if so configured). At step 430, the web server 42 updates the PHP web page with the new information. The web server 42 may retrieve the patient-related information from the shadow server 50 in XML format as shown in block 432. Similarly, the web server 42 may retrieve the patient-created information from the PHR data server 12 in XML format, the patient-created information including user-entered notes or messages.

The system 10 provides ability for the user to send and receive secure messages to the user's health care providers and administrators. Selecting the link 230 in FIG. 2 initiates a secure messaging routine 500 illustrated in FIG. 5. The message types include a request for medical advice; a request for prescription renewal; a request for a referral; a customer service request; a request for a pre-qualified appointment and a request for an appointment, and the user selects the message type by selecting an appropriate link associated with the message type represented by blocks 502-512, respectively. Responsive to the user selecting one of the links 502-512, at step 514, the web server 42 creates a secure messaging form on the PHP web page for the selected message type. At step 516, the user enters the appropriate data and information into the message form. The user may cancel the message, step 518, and be returned to the previous PHP web page, or the user clicks send, step 522. The web server 42 forwards the information to the PHR server 12, step 524, and the PHR server 12 places the user's message in a queue for transmission to the EHIS data server 14. At step 528, the EHIS data server 14 receives the incoming message from the queue, and translates and routes the message to the appropriate destination, and at step 530, the web server 42 updates the PHP web page to reflect that the user's message has been sent.

Selecting the link associated with block 232 (FIG. 2) allows the user to add notes to the patient-created information, and selecting the link associated with the block 234 allows the user to complete forms. Selecting either link 232 or 234 initiates a process 600 illustrated in FIG. 6. Additionally, the user may add information flags to the patient-created information and/or other information contained with the PHR server 12. The information flag identifies the flagged information and may provide read only access of the information to one or more of the user's health care professionals and staff. Coupled with the information flag, the PHR server 12 is adapted to generate an alert that is communicated to the EHIS data server 14 indicating the receipt of the flag. Appropriate messaging may also be generated and communicated to the one or more of the user's health care professionals and staff.

If the user has selected the link associated with block 232, the web server 42 creates an add/edit notes form and displays the form on the PHP web page. At step 604, the user enters or edits the note text in an editing window. If the user selects cancel, step 606, the notes/edits are discarded and the web server 42 returns to the previously displayed PHP web page. If the user clicks to save changes, step 610, the web server 42 forwards the edited text to the PHR data server 12, step 612, and the PHR data server 12 updates the patients notes portion of the patient-created date stored within the PHR data server 12, step 614. The user notes may be unstructured information, such as unstructured text notes, or the notes may be structured information. As an example, to input structured information the user may be presented with a form seeking particular information, such as medications they are currently taking or procedures they have had or will have. The fields within the form may be linked to other data entries in the enterprise health record system, such as reference materials for the entered medication or procedure. Moreover, the information need not be clinical in nature, as described in foregoing examples, but may be administrative in nature, such as benefits information.

A similar process occurs if the user has selected the link associated with block 234. The web server 42 creates an online form, such as an insurance form or medical history form, and displays the form on the PHP web page, step 616. At step 618, the user enters information into the form in an editing window. If the user selects cancel, step 620, the information and form are discarded and the web server 42 returns to the previously displayed PHP web page, step 608. If the user clicks to save changes, step 622, the web server 42 forwards the edited form to the PHR data server 12, step 624, and the PHR data server 12 forwards the information from the edited form to the EHIS server 50, step 626, where it is processed appropriately. The web server 42 then returns the user to the previous PHP web page, step 608.

Figure 7:
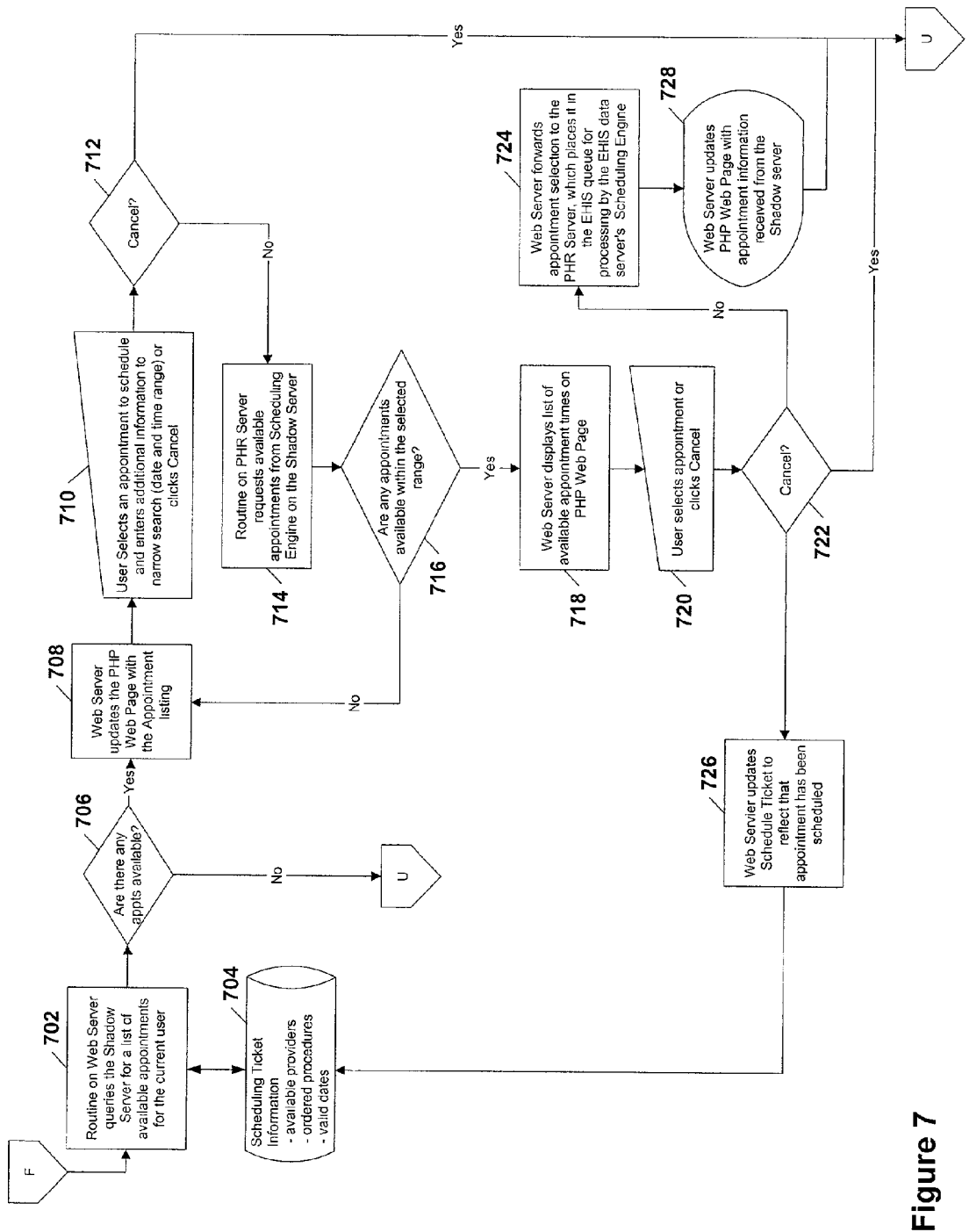
FIG. 7 is a flowchart illustrating operation of the system illustrated in FIG. 1 for scheduling appointments in accordance with a preferred embodiment of the invention.

By selecting the link associated with the block 236 (FIG. 2) the user may schedule a prequalified appointment in accordance with a process 700 illustrated in FIG. 7. Upon selecting the link, the web server 42 queries the shadow server 50 for a list of available appointments for the current user, step 702. Whether prequalified appointments are available will depend on the existence of a scheduling ticket illustrated at 704. The scheduling ticket is provided by the shadow server 50 responsive to input received from a care provider and specifies which providers are available, what procedures are required and dates and times that the appointment may be scheduled. If there are appointments available, step 706, the web server 42 updates the PHP web page with a listing of the appointments, step 708. At step 710, the user selects an appointment to schedule and, if necessary, provides additional information necessary to narrow the search for dates, times, etc. The user may also cancel the process at step 712, and web server 42 returns the user to the PHP web page. Otherwise, at step 714, the PHR data server 12 requests available appointments from a scheduling engine portion (not depicted) of the shadow server 50. If there are no appointments that meet the user specified criteria, step 716, the web server 42 updates the PHP web page, and the user is requested to enter revised information. Otherwise, at step 718 the web server 42 displays the list of available appointment times on the PHP web page. At step 720, the user selects an appointment, and the web server 42 forwards the appointment selection to PHR data server 12, which places the request in the EHIS queue 16 for processing by the EHIS data server 14. When the appointment is booked, the updated appointment information flows via the shadow server 54 from the EHIS data server 14 to the web server, which updates the PHP web page with the selected appointment summary information, step 728. The web server 42 also updates the scheduling ticket to reflect that a prequalified appointment has been scheduled. The user may otherwise cancel the scheduled appointment at step 722 and be returned to the PHP web page.

Figure 8:
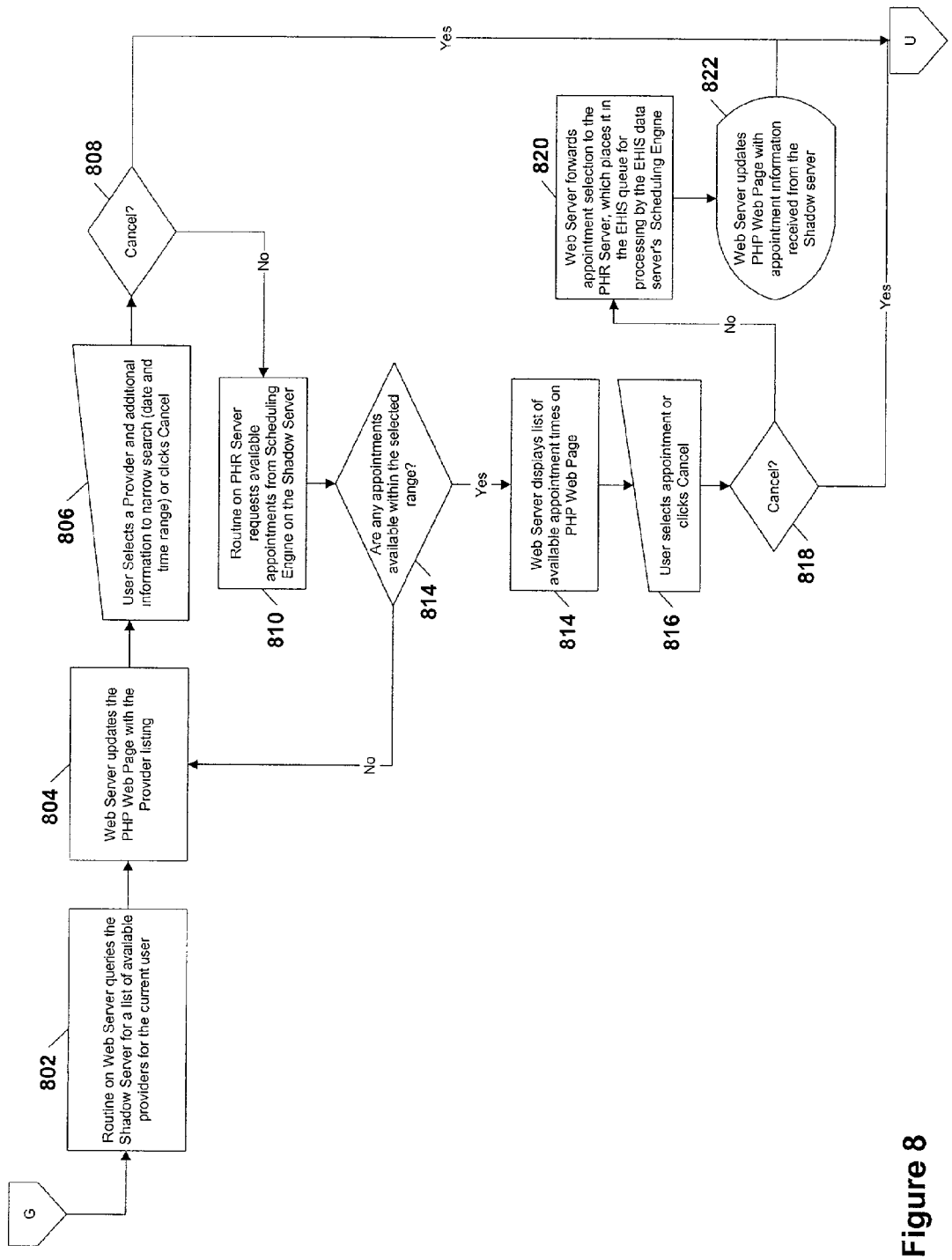
FIG. 8 is a flowchart illustrating operation of the system illustrated in FIG. 1 for scheduling appointments in accordance with another preferred embodiment of the invention.

A second appointment option is initiated by selecting the link associated with block 238 (FIG. 2), which starts a process 800 illustrated in FIG. 8. After the user selects the link 238, the web server 42 queries the shadow server 50 for a list of available providers for the user, step 802. At step 804, the web server 42 updates the PHP web page with a list of the providers. At step 806, the user selects a provider and provides additional information, such as dates and times for the appointment. The user may also cancel, step 808, and the web server 42 returns the user to the PHP web page. Otherwise, at step 810 the PHR data server 12 requests available appointments information from the scheduling engine portion of the shadow server 50. If there are no appointments within the date and time range provided by the user, step 812, the web server 42 updates the PHP web page for the user to provide additional information. Otherwise, the web server 42 updates the PHP web page with a list of the available appointments, step 814. At step 816, the user selects an appointment or cancels the process, step 818. If an appointment is requested, the web server 42 forwards the appointment information to the PHR data server 12, which places the information in the EHIS queue 16 for processing by the EHIS data server 14. When the appointment is booked, the updated appointment information flows via the shadow server 54 from the EHIS data server 14 to the web server, which updates the PHP web page with the selected appointment summary information, step 822.

Figure 9:
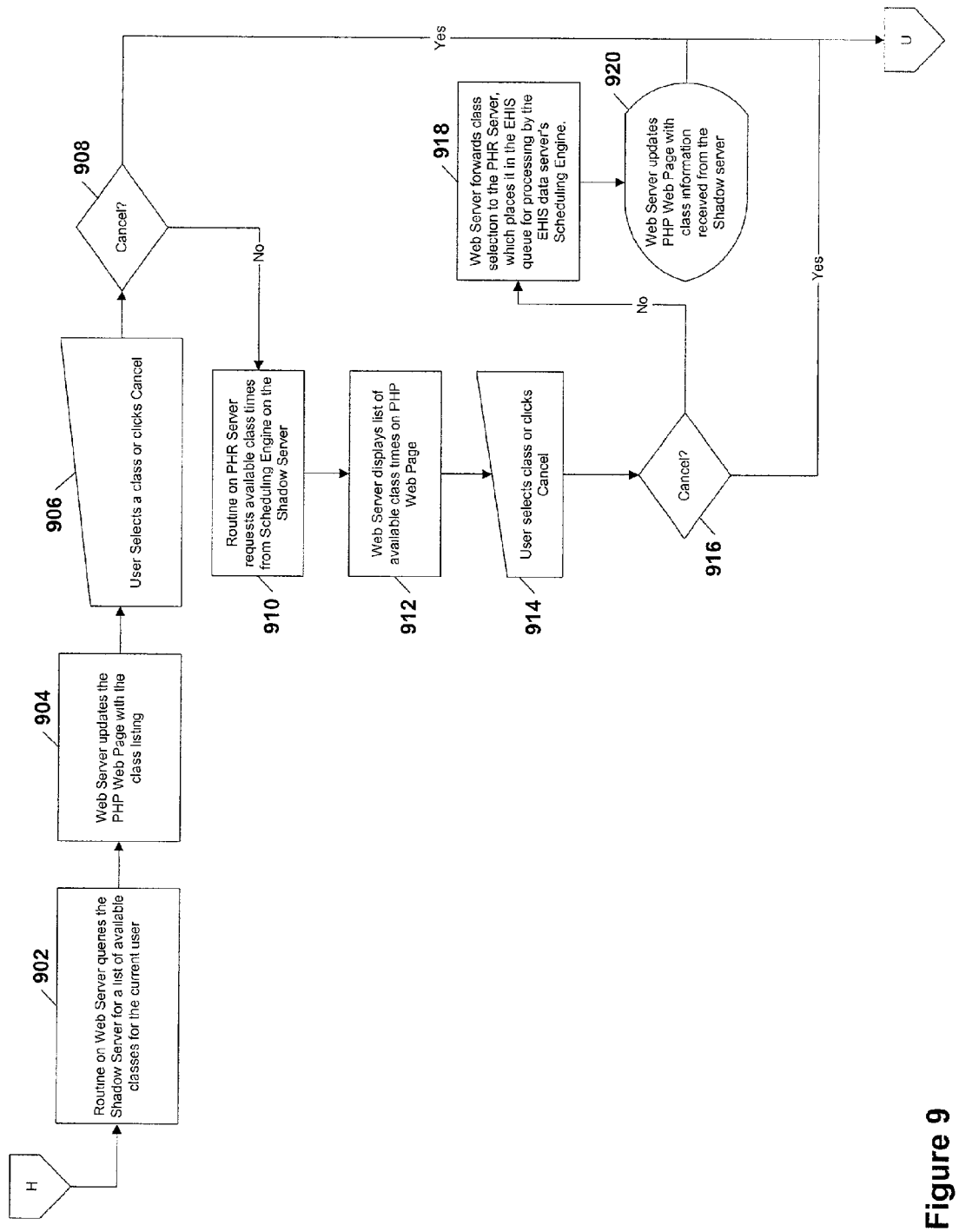
FIG. 9 is a flowchart illustrating operation of the system illustrated in FIG. 1 for providing class enrollment.

By the user selecting the link associated with block 240 (FIG. 2) a process 900 illustrated in FIG. 9 is started that allows the user to enroll in a class. After the user selects the link 240, the web server 42 queries the shadow server 50 for a list of available classes for the user, step 902. At step 904, the web server 42 updates the PHP web page with a list of the classes. At step 906, the user selects a class or cancels the process, step 908. If the user cancels the process, the web server 42 returns the user to the PHP web page. Otherwise, at step 910 the PHR data server 12 requests available class times from the scheduling engine portion of the shadow server 50. At step 912, the web server 42 displays the list of available class times, and at step 914 the user selects a class time or cancels. If an appointment is requested, the web server 42 forwards the appointment information to the PHR data server 12, which places the information in the EHIS queue 16 for processing by the EHIS data server 14. When the appointment is booked, the updated appointment information flows via the shadow server 54 from the EHIS data server 14 to the web server, which updates the PHP web page with the selected appointment summary information, step 920. If the process is cancelled, the web server 42 returns the user to the PHP web page.

Figure 10:
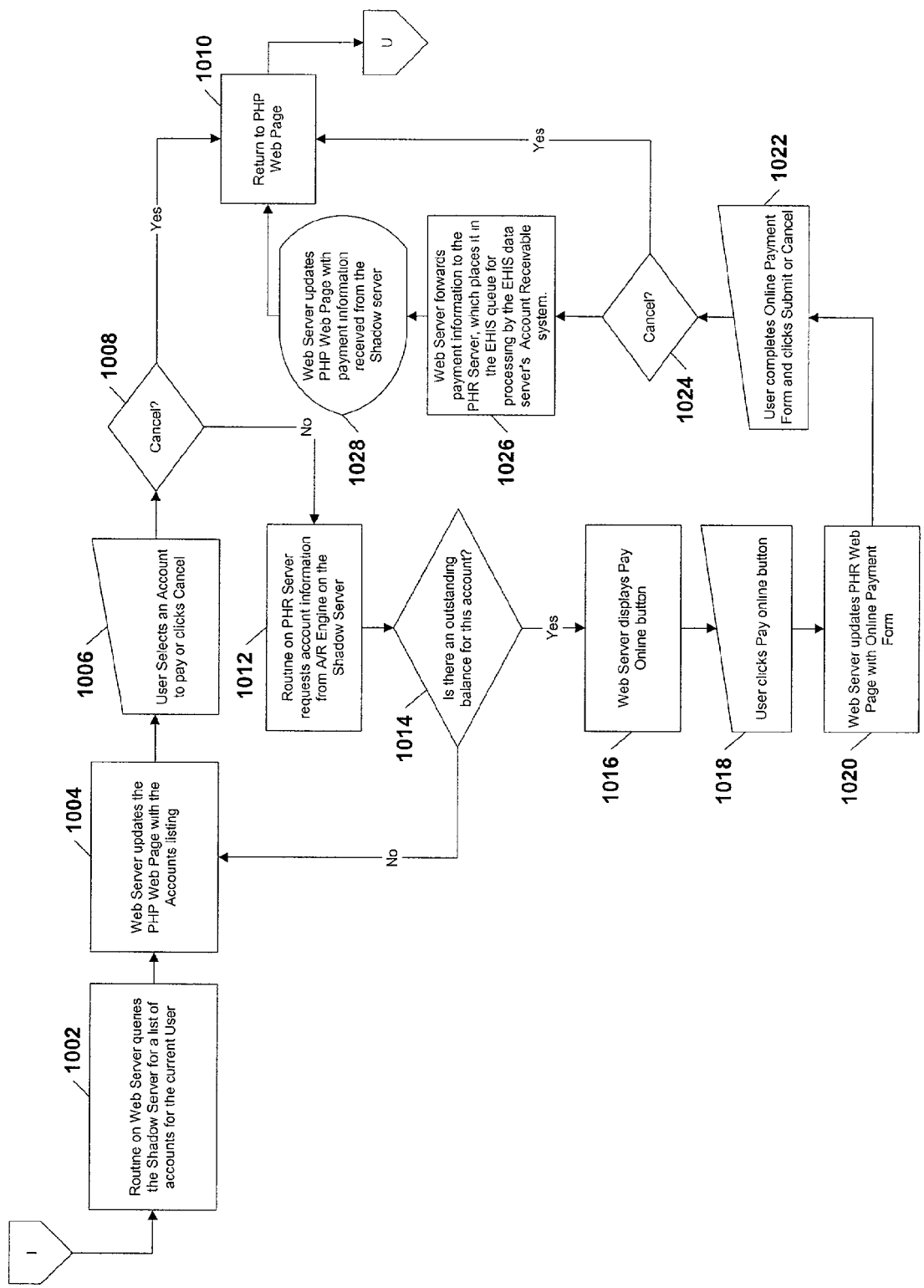
FIG. 10 is a flowchart illustrating operation of the system illustrated in FIG. 1 for paying bills.

By selecting the link associated with the block 242 (FIG. 2) the user may initiate a process 1000 illustrated in FIG. 10 for paying a bill. The process 1000 begins at step 1002 with the web server 42 making a query of the shadow server 50 for accounts for the user. The web server 42 at step 1004 updates the PHP web page with an accounts listing. The user may select an account at step 1006, or may cancel, step 1008. If the user cancels, the web server 42 returns the user to the PHP web page, step 1010. If the user does select an account, at step 1012 a routine on the PHR data server 12 requests information from an accounts receivable engine portion (not depicted) of the shadow server 50. The account is checked to determine if there is an outstanding balance, step 1014. The user may then return to the PHP web page providing the account listing. The user may elect to pay all or a portion of any balance due or may elect to pay ahead to develop an account credit toward an upcoming procedure. To permit the user to make a payment, the web server 42 displays a pay online option for the account, step 1016. The user may click the pay online option, step 1018, and the web server updates the PHP web page with an online payment form, step 1020. The user completes the online payment form, step 1022, or the user may cancel the process, step 1024 and be returned to the PHP web page. At step 1026, the web server 42 forward the information from the completed payment form to the PHR data server 12, which places the information in the EHIS queue 16 for processing by the EHIS data server 14. When the payment is processed by the EHIS data server, the information flows via the shadow server to the web server 42, which updates the PHP web page 38 with a message indicating that the payment has been submitted, step 1028. The invention has been described in terms of several preferred embodiments, including a number of features and functions. Not all features and functions are required for every embodiment of the invention, and in this manner the invention provides a flexible system by which a user may access patient records, send and receive messages, retrieve information, schedule appointments, renew prescriptions, pay bills and the like. The features discussed herein are intended to be illustrative of those features that may be implemented; however, such features should not be considered exhaustive of all possible features that may be implemented in a system configured in accordance with the preferred embodiments of the invention.

We claim:

1. A computer system allowing patient-sourced data to be added to a clinical medical record system comprising:
   a computer-implemented clinical medical record database created by and accessible to healthcare providers and holding clinical information generated by the healthcare providers during the provision of healthcare, wherein the healthcare providers have write access to a clinical medical record and a patient described in the clinical medical record does not have write access to the clinical medical record;
   a computer-implemented personal health record database holding patient-sourced medical data entered by the patient; and
   a computer-implemented Web portal configured to control access to both of the clinical medical record database and the personal health record database and operating in one of:
   (1) a first mode in which the patient is provided with access to the patient-sourced medical data in the personal health record database but not data of the clinical medical record when the patient provides basic identification information including a user name and password that are not linked to the clinical medical record; and
   (2) a second mode in which the patient is provided with access to the patient-sourced medical database and read-only access to the data of the clinical medical record based on a prior determination that the user is a patient of the healthcare provider and creation of a computer-implemented link between the user name and password and the clinical medical record.

2. The computer system of claim 1 wherein the second mode allows integrated access of the personal health record database including the patient-sourced data and data of the clinical medical record database by the patient without re-entry of information from the personal health record database by the patient.

3. The computer system of claim 1 wherein the Web portal in the second mode allows the user to flag patient-sourced data wherein the flagged data is accessible by the healthcare provider.

4. The computer system of claim 1 wherein in the Web portal in the first mode allows the patient to undertake electronic communication with healthcare professionals.

5. The computer system of claim 1 wherein the patient provides a user name and identifying information that is anonymous in nature in the first mode.

6. The computer system of claim 1 wherein the Web portal in the first mode does not permit the patient to make appointments with the healthcare professionals and the Web portal in the second mode does allow the patient to make appointments with health care professionals.

7. A method of operating a computer system to allow patient-sourced data to be added to a clinical medical record created by and accessible to healthcare providers holding clinical information, the method comprising the steps of:
   receiving a selection of a first mode or a second mode wherein the second mode is selectable based on a prior determination that the user is a patient of the healthcare provider indicated by a computer implemented link between an identification of the user and a clinical medical record for that user and the first mode requires the identification of the user but does not require authentication of the identity of the user; and
   executing a program on a Web portal communicating with the clinical medical record to accept patient-sourced medical data from the patient for inclusion in a personal health record database and to operate based on the selection in one of:
   (1) the first mode in which the patient is provided with access to the personal health record database including the patient-sourced medical data but not data of the clinical medical record in the clinical medical record; and
   (2) the second mode in which the patient is provided with access to the personal health record database including the patient-sourced medical data and read-only access to the data of the clinical medical record in the clinical medical record when the patient has been determined to be a patient of the healthcare provider.

8. The method of claim 7 wherein the second mode allows integrated access of both patient-sourced data and data of the clinical medical record by the patient without re-entry of information by the patient.

9. The method of claim 7 wherein the second mode allows the user to flag patient-sourced data wherein the flagged data is accessible by the healthcare provider.

10. The method of claim 7 wherein in the Web portal in the first mode allows the patient to undertake electronic communication to ask questions of the healthcare professionals.

11. The method of claim 7 wherein the patient provides a user name and identifying information that is anonymous in nature in the first mode.

12. The method of claim 7 wherein the Web portal in the first mode does not permit the patient to make appointments with the healthcare professionals and the Web portal in the second mode does allow the patient to make appointments with health care professionals.

13. A computer system allowing patient-sourced data to be added to a clinical medical record system comprising:
   a computer-implemented clinical medical record database created by and accessible to healthcare providers holding clinical information, wherein the healthcare providers have write access to a clinical medical record and a patient described in the clinical medical record does not have write access to the clinical medical record;
   a computer-implemented personal health record database holding patient-sourced medical data entered by the patient; and
   a computer-implemented Web portal configured to control access to both of the clinical medical record database and the personal health record database and accepting patient-sourced medical data from the patient in a first mode in which the patient is provided with access to the personal health record database and the patient-sourced data by providing a user name and password but not provided with permission to make appointments and request services of the healthcare providers when the patient is not fully identified as a patient of the healthcare provider,
   the Web portal including an option to convert to a second mode wherein the patient-sourced data is incorporated into the clinical medical record when the patient has registered and a computer implemented link between the user name and password and the clinical medical record has been created and thus is fully identified and wherein the patient is permitted to make appointments and request services of the healthcare providers.

14. The computer system of claim 13 wherein the second mode allows integrated access to the personal health record database including the patient-sourced data and to the data of the clinical medical record by the patient without re-entry of information by the patient.

15. The computer system of claim 13 wherein the Web portal in the second mode allows healthcare professionals to view selected patient-sourced data flagged by the patient.

16. The computer system of claim 13 wherein in the Web portal in the first mode allows the patient to undertake electronic communication with healthcare professionals.

17. The computer system of claim 13 wherein the patient provides a user name and identifying information that is anonymous in nature in the first mode.

18. The computer system of claim 13 wherein the Web portal in the first mode does not permit the patient to make appointments with the healthcare professionals and the Web portal in the second mode does allow the patient to make appointments with health care professionals.

* * * * *